(12) United States Patent
Lin et al.

(10) Patent No.: US 8,702,763 B2
(45) Date of Patent: Apr. 22, 2014

(54) IN-SITU DEFORMABLE MINI-BONE PLATE

(76) Inventors: Jiin-Huey Chern Lin, Winnetka, IL (US); Chien-Ping Ju, Kansas City, MO (US); Jing-Wei Lee, Tainan (TW)

( * ) Notice: Subject to any disclaimer, the term of this patent is extended or adjusted under 35 U.S.C. 154(b) by 137 days.

(21) Appl. No.: 13/531,710

(22) Filed: Jun. 25, 2012

(65) Prior Publication Data

US 2012/0330365 A1  Dec. 27, 2012

Related U.S. Application Data

(60) Provisional application No. 61/501,340, filed on Jun. 27, 2011.

(51) Int. Cl.
*A61B 17/80* (2006.01)
(52) U.S. Cl.
USPC .......................................... 606/284; 606/285
(58) Field of Classification Search
USPC ................................................. 606/283–285
See application file for complete search history.

(56) References Cited

U.S. PATENT DOCUMENTS

| 5,746,742 A | * | 5/1998 | Runciman et al. | 606/86 B |
| 5,752,958 A | * | 5/1998 | Wellisz | 606/285 |
| 6,364,881 B1 | * | 4/2002 | Apgar et al. | 606/284 |

* cited by examiner

*Primary Examiner* — Andrew Yang
(74) *Attorney, Agent, or Firm* — Bacon & Thomas, PLLC

(57) ABSTRACT

A bone plate provided in the present invention has an elongated strip, and a series of repeating units are provided on the elongated strip. Each repeating unit has two crowns, two necks, and four bridges, wherein the two crowns and the two necks are connected by the four bridges to from a symmetrical ring structure, and wherein a width of the bridge (BW) is greater than a width of the crown (CW), a maximum distance between inner sides of the two crowns (ID) is greater than a width of the neck (NW), a maximum distance between outer sides of two opposite bridges of the four bridges (OD) is greater than a unit length between two adjacent repeating units (UL), and the crown width (CW) is 0.1-1.0 mm, so that the bone plate can be deformed in-situ by a surgeon.

14 Claims, 7 Drawing Sheets

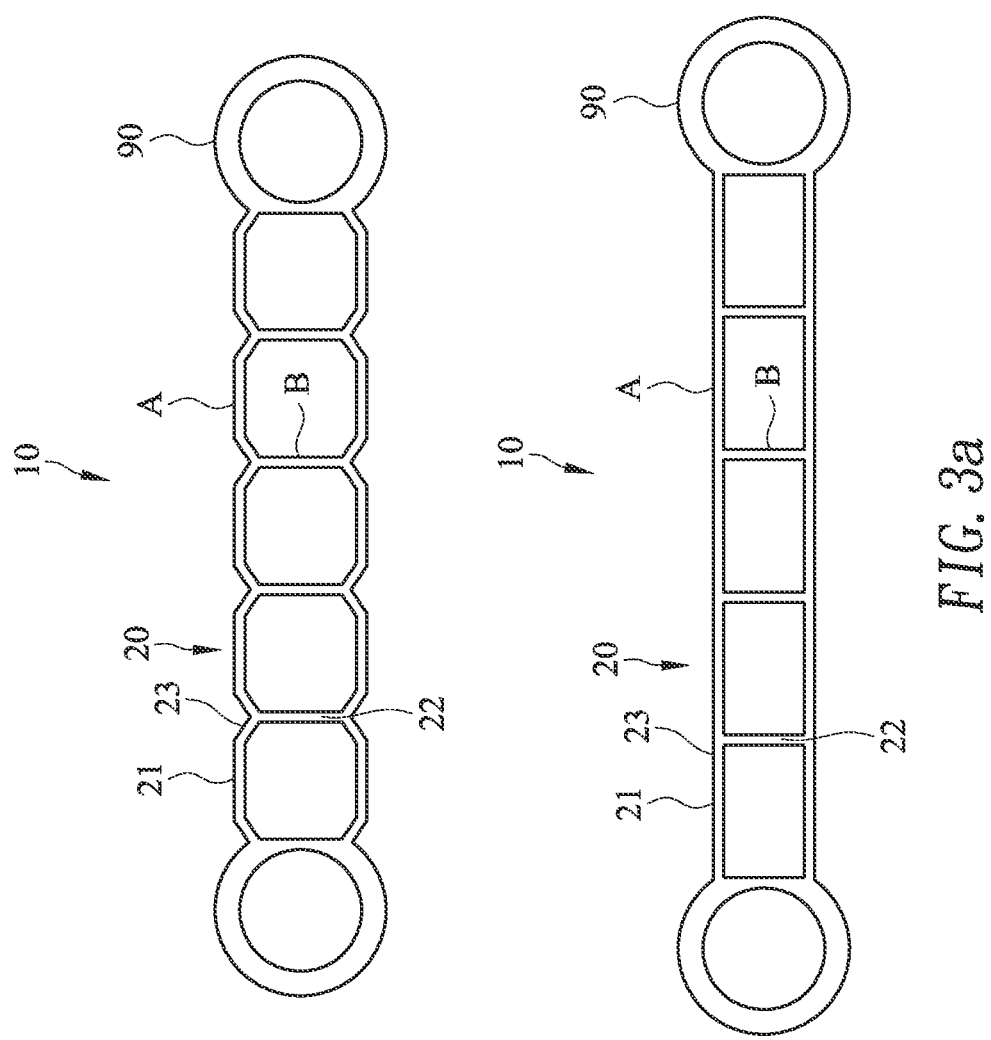

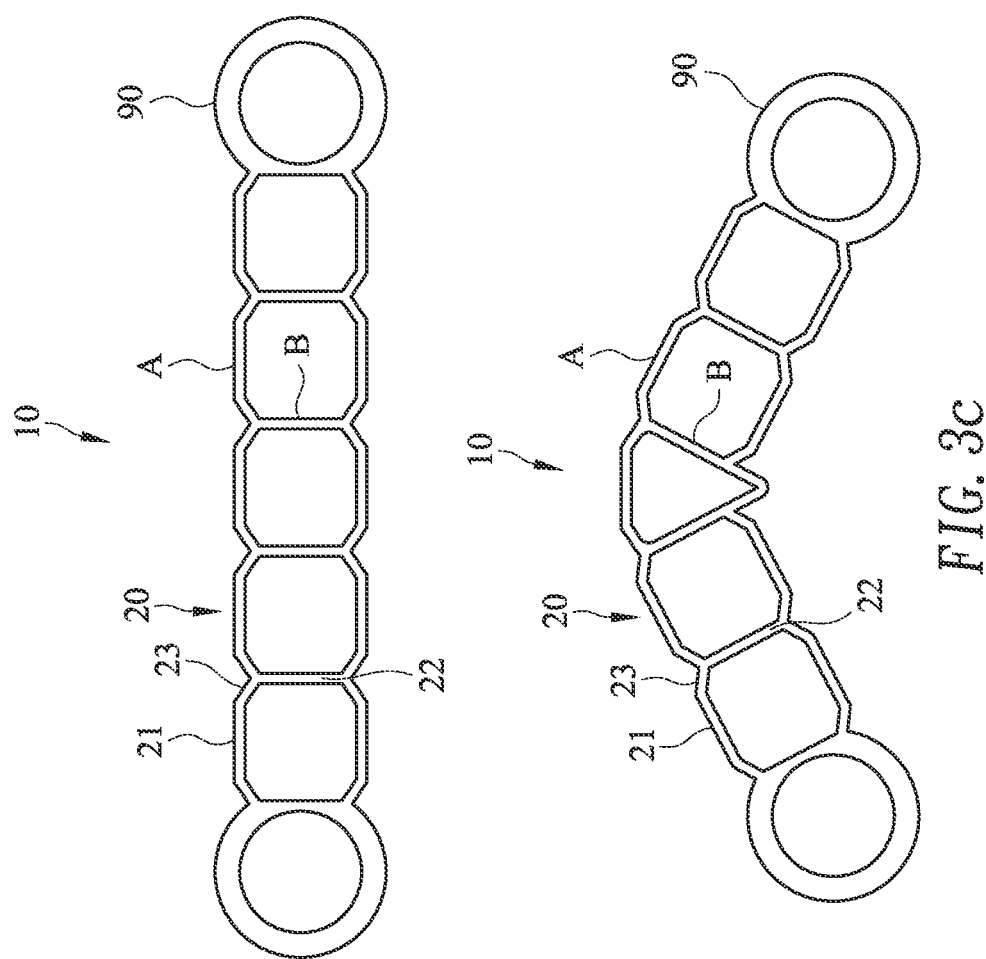

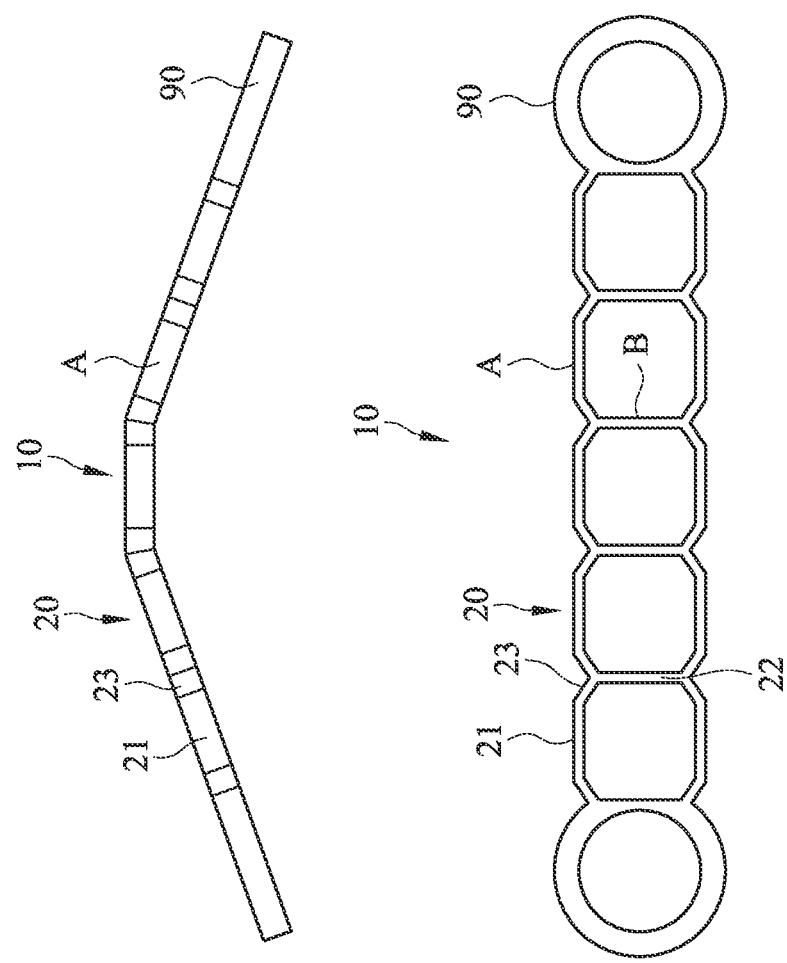

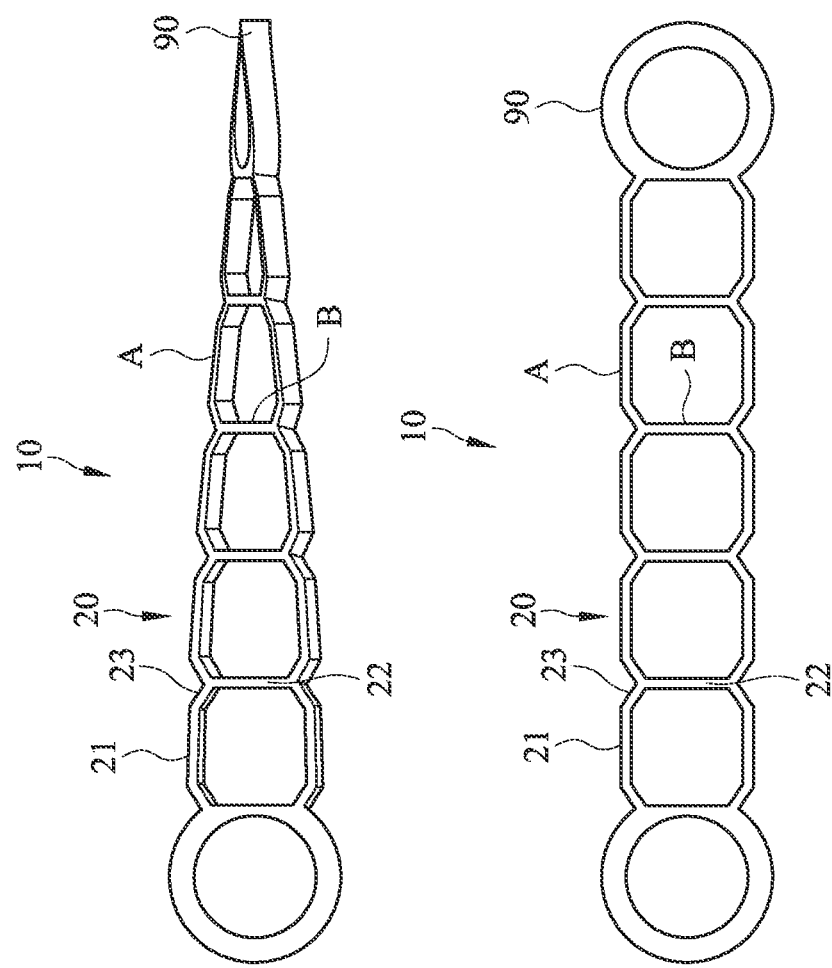

IN-SITU DEFORMABLE MINI-BONE PLATE

CROSS REFERENCE TO RELATED PATENT APPLICATIONS

The present patent application claims the benefit of U.S. provisional patent application No. 61/501,340, filed Jun. 27, 2011, the contents of which are hereby incorporated by reference in their entireties.

FIELD OF THE INVENTION

The present invention is related to the field of orthopaedic implants. In particular, the present invention provides a bone plate which is easy to be deformed in-situ to match the natural or desired reconstructed shape of the bone surface during surgery operations.

BACKGROUND OF THE INVENTION

During many surgical procedures for fixing fractured bones using plates and screws, the bone plates in use very often need to be deformed in-situ to facilitate the complicated, often three-dimensional fracture geometries.

Conventionally, and very often, some screws and plates which have already been fixed in place need to be removed, deformed using some common tools such as clamps, and re-screwed into the fractured bone. This frustrating process does not guarantee success, especially when complicated shape, multiple fractures are involved in the procedures. If not successful, the screwing/unscrewing process has to be repeated. Not only time-consuming, this screwing/unscrewing process can further damage the already weakened fractured bones and increase the risks of the procedures.

U.S. Pat. No. 5,746,742 discloses a bone plate template which is an easily contourable plate that is placed against a bone, and contoured using finger pressure. After it is contoured by a clinician, it is used by a technician to create a duplicate contoured bone plate for implantation. The template must, therefore, resemble its corresponding bone plate in all material aspects. Therefore, most templates are simply a silhouette of their corresponding bone plate. Such prior art templates, made from a relatively soft material such as aluminum, may still require substantial force to deform, especially to arc, which is not desirable in a confined surgical environment. Moreover, it has been observed that when soft material such as aluminum is used in a template, attempts at arcing may result in folding or kinking of the template, in the notch region. The inventors of U.S. Pat. No. 5,746,742 discover that this particular phenomena tends to disappear if the width to thickness ratio of the material of the template is kept below about 1.6:1, preferable about 1.5:1, but as low as about 1.4:1. However, the commonly encountered problem that fractured bone pieces often move during fixation (e.g. drilling) cannot be overcome according to the technique disclosed in U.S. Pat. No. 5,746,742.

SUMMARY OF THE INVENTION

A primary objective of the present invention is to provide a bone plate for affixing fractured bones with the help of bone screws, and the bone plate is relatively easy to be deformed to match the natural or desired reconstructed shape of the bone surface, so that fractured bones can be reconstructed and affixed according to the shape desired by the surgeon. The "relatively easy" used hereinafter intends to mean that the bone plate can be deformed by the surgeon with the orthopaedic tools during the operation, and even after the bone plate has been fixed to fractured bones by bone screws, i.e. the bone plate can be deformed in-situ by the surgeon through the incision.

Another objective of the present invention is to provide a bone plate, which is relatively easy to be shortened or lengthened.

Still Another objective of the present invention is to provide a bone plate, which is relatively easy to be shortened, lengthened, bended, arched or twisted.

In order to accomplished the aforesaid objectives a bone plate constructed in accordance with the present invention comprises a first elongated strip comprising a first series of repeating units, a first and a second terminal screw holes being provided at two ends of the first series of the repeating units, wherein the number of the repeating unit between the two terminal screw is about 2-20, and each repeating unit comprises two crowns, two necks, and four bridges, wherein the two crowns and the two necks are connected by the four bridges to from a ring structure, characterized in that a maximum distance between inner sides of the two crowns (ID) is greater than a width of the neck (NW), and a maximum distance between outer sides of two opposite bridges of the four bridges (OD) is greater than a unit length between two adjacent repeating units (UL), which is a distance between centers of two neighboring ring structures.

Preferably, a width of the bridge (BW) is greater than a width of the crown (CW).

Preferably, an outer side of each of the two crowns of the repeating unit is faceted.

Preferably, inner sides of each of the two necks of the repeating unit are faceted.

Preferably, the bone plate of the present invention further comprises a second elongated strip with one end thereof extending or branching from the first elongated strip and with another end thereof being provided with a third terminal screw hole, wherein the second elongated strip comprises a second series of the repeating units between the first elongated strip and the third terminal screw hole. More preferably, the second elongated strip and the first elongated strip have a common longitudinal axis. Alternatively, the first elongated strip has a first longitudinal axis, and the second elongated strip has a second longitudinal axis, wherein the second elongated strip extends from one of the first or the second terminal screw hole with the first longitudinal axis and the second longitudinal axis forming an obtuse angle therebetween, or the first elongated strip and the second elongated strip form a shape similar to y.

Preferably, the bone plate of the present invention further comprises a second elongated strip with one end thereof extending or branching from the first elongated strip and with another end thereof being provided with a third terminal screw hole; and a third elongated strip with one end thereof extending or branching from the first elongated strip and with another end thereof being provided with a fourth terminal screw hole, wherein the second elongated strip comprises a second series of the repeating units between the first elongated strip and the third terminal screw hole, and the third elongated strip comprises a third series of the repeating units between the first elongated strip and the fourth terminal screw hole. More preferably, the first elongated strip, the second elongated strip and the third elongated strip form a shape similar to Y, X, T, + or π.

Preferably, the first elongated strip has a thickness of about 0.1-2.5 mm, the CW is about 0.1-1.0 mm, the BW is of about 0.2-3.5 mm, the ID is of about 1-8 mm, the NW is about 0.5-5 mm, the OD is about 1.5-15 mm, and the UL is about 1-10 mm.

More preferably, the first elongated strip has a thickness of about 0.5-1.5 mm, the CW is about 0.1-0.5 mm, the BW is of about 0.2-2 mm, the ID is of about 2-4 mm, the NW is of about 1-3 mm, the OD is of about 2.5-5 mm, and the UL is of about 2-5 mm.

Preferably, the first elongated strip is made of a metal of pure titanium, titanium alloy, pure iron, iron alloy, pure magnesium, magnesium alloy, pure zinc, zinc alloy, or a composite prepared from at least two of these metals.

The present invention further discloses a method of deforming a bone plate of the present invention, which comprises shortening the bone plate or lengthening the bone plate, wherein said shortening the bone plate comprises the following steps:

squeezing the ring structure of one repeating unit of the first series of the repeating units by clamping the two necks of the ring structure, so that the two crowns between the clamped two necks are arched in a direction perpendicular to a longitudinal axis of the first elongated strip and on a same plane of the first elongated strip; and repeating the squeezing step to another repeating unit of the first series of the repeating units until a desired number of the repeating units of the first series of repeating units are squeezed; and said lengthening the bone plate comprises the following steps:

flattening the ring structure of one repeating unit of the first series of the repeating units by clamping the two crowns of the ring structure, so that the clamped two crowns and the four bridges of the same ring structure are flattened on a same plane of the first elongated strip; and repeating the flattening step to another repeating unit of the first series of the repeating units until a desired number of the repeating units of the first series of repeating units are flattened.

Preferably, the method of the present invention further comprises bending the bone plate, or twisting the bone plate, wherein said bending the bone plate comprises the following steps:

inserting three posts into three ring structures of the first series of the repeating units; and pulling two end posts of the three posts in a first direction perpendicular to a longitudinal axis of the first elongated strip and on a same plane of the first elongated strip and simultaneously pushing a middle post of the three posts in a second direction opposite to the first direction, so that the two crowns of the ring structure receiving the middle post are bended; and said twisting the bone plate comprises the following steps:

clamping both ends of the first elongated strip; and rotating one end of the first elongated strip while holding another end thereof still, so that the first elongated strip is twisted.

BRIEF DESCRIPTION OF THE DRAWINGS

FIG. 3a shows the lengthening of the bone plate shown in FIG. 2.

FIG. 3c shows the in-plane bending of the bone plate shown in FIG. 2.

FIG. 3d shows the out-of-plane bending of the bone plate shown in FIG. 2.

FIG. 3e shows the twisting of the bone plate shown in FIG. 2.

DETAILED DESCRIPTION OF THE INVENTION

Figure 1:
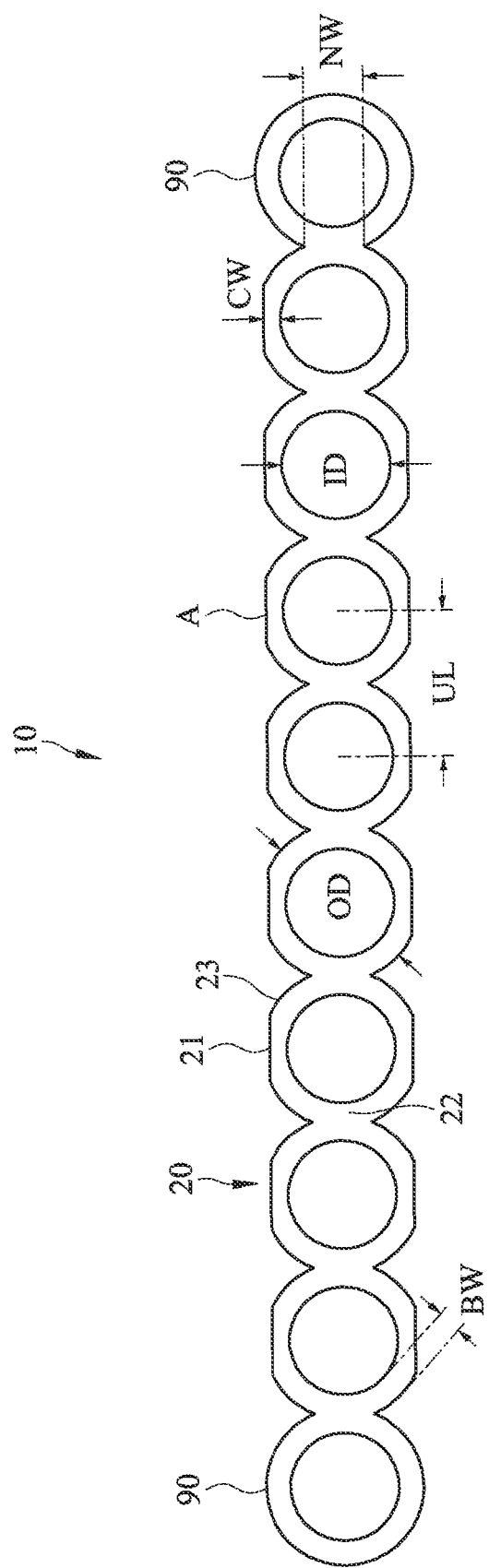
FIG. 1 shows an illustrated top plan view of a bone plate constructed according to one preferred embodiment of the present invention.

A bone plate of an elongated strip 10 constructed according to one of the preferred embodiments of the present invention is shown in FIG. 1, which has eight repeating units of a faceted ring structure 20, and two terminal screw holes 90. In addition to the two terminal screw holes 90 any one of the faceted ring structures between the two terminal screw holes 90 can also be used as an auxiliary screw hole. Moreover, the elongated strip 10 may be provided with one or more terminal screws adjacent to the terminal screw hole 90, if it is required.

Each faceted ring structure 20 is formed by two crowns 21, two necks 22, and four bridges 23 connecting the two crowns 21 to the two necks 22.

The faceted ring structure 20 can be deformed in-situ by a mechanical force, and manipulated into a shape as desired. It is discovered that, in order to be easily manipulated as desired, the crown 21 has a crown width (CW) which is smaller (preferably smaller by at least 20%) than a bridge width (BW) of the bridge 23.

It is further discovered that, in order to be easily manipulated as desired, the faceted ring structure 20 should have an inner diameter (ID), i.e. a maximum distance between inner sides of the two crowns, greater (preferably greater by at least 20%) than a neck width (NW) of the neck 22.

It is further discovered that, in order to be easily manipulated as desired, the elongated strip 10 of the bone plate should preferably have at least two adjacent faceted ring structures 20 having a unit length (UL) smaller (preferably smaller by at least 20%) than an outer diameter (OD) of the two adjacent faceted ring structures 20. The outer diameter (OD) is a maximum distance between outer sides of two opposite bridges 23 of the faceted ring structure 20, and the unit length (UL) is a distance between centers of two neighboring symmetrical ring structures 20.

It is further discovered that, in order to be easily manipulated as desired, the ID of the faceted ring structure 20 is at least 50% (preferably at least 60%) of the OD of the faceted ring structure 20 (ID>½ OD). More specifically, the crown width (CW) is about 0.1-1.0 mm. Preferably, the faceted ring structure 20 has faceted and substantially flat surface A at the outer side of each of the two crowns 21.

For lengthening the bone plate shown in FIG. 1, one can flatten the faceted ring structure 20 by clamping the two crowns 21, so that the clamped two crowns 21 and the four bridges 23 of the same faceted ring structure are flattened on a same plane of the elongated strip 20; and repeat the flattening step to another faceted ring structure 20 until a desired number of the faceted ring structures 20 are flattened.

For shortening the bone plate, one can squeeze the faceted ring structure 20 by clamping the two necks 22, so that the two crowns 21 between the clamped two necks are arched in a direction perpendicular to a longitudinal axis of the elongated strip and on a same plane of the elongated strip; and repeat the squeezing step to another faceted ring structure 20 until a desired number of the faceted ring structures 20 are squeezed.

For in-plane bending the bone plate, one can insert three posts into three faceted ring structures 20; pull two end posts of the three posts downwardly while simultaneously pushing a middle post of the three posts upwardly, so that the two crowns of the symmetric ring structure receiving the middle post are bended.

For out-of-plane bending the bone plate, one can insert a hook into one faceted ring structure 20 located at a middle section of the elongated strip 10; and pull the hook in a out-of-plane direction while the two terminal screw holes 20 being fastened, so that the elongated strip is arched in a out-of-plane direction.

For twisting the bone plate, one can clamp both ends of the elongated strip 10; and rotate one end of the elongated strip 10 while holding another end thereof still, so that the elongated strip is twisted.

Figure 2:
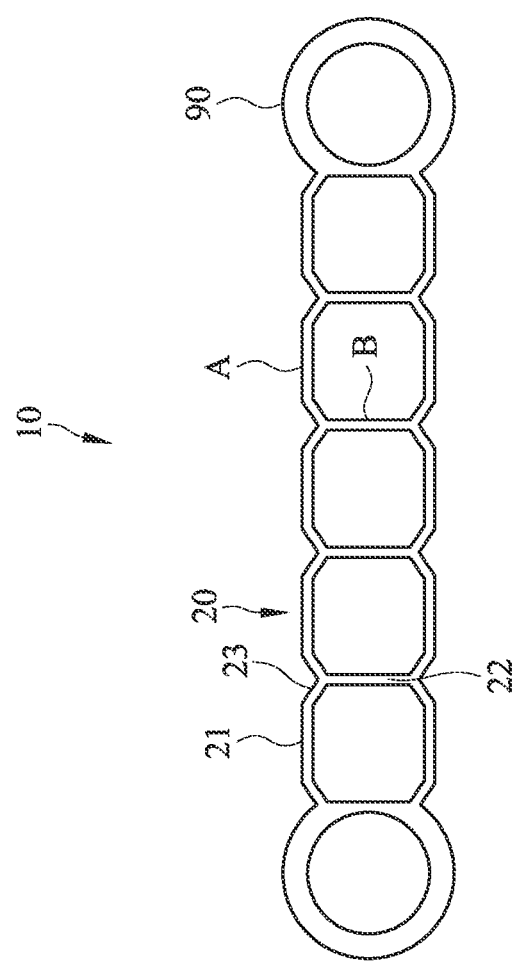
FIG. 2 shows an illustrated top plan view of a bone plate constructed according to another preferred embodiment of the present invention.

In the present invention the faceted ring structure 20 has a ring shape but not necessarily a round shape. A bone plate similar to the bone plate shown in FIG. 1 and constructed according to another preferred embodiment of the present invention is shown in FIG. 2, wherein like elements or parts between the two embodiments are represented by like numerals. The bone plate shown in FIG. 2 is further provided with a faceted and substantially flat surface B at the inner sides of the necks 22 of the faceted ring structure 20.

The bone plate shown in FIG. 2 has a thickness of about 1.2 mm, wherein the crown width (CW) is 0.5 mm, the width of the bridge (BW) is of 0.6 mm, the maximum distance between inner sides of the two crowns (ID) is of 2.2 mm, the width of the neck (NW) is of 2 mm, the maximum distance between the outer sides of the two opposite bridges (OD) is of 3.4 mm, and the unit length (UL) is of 2.5 mm.

Figure 3B:
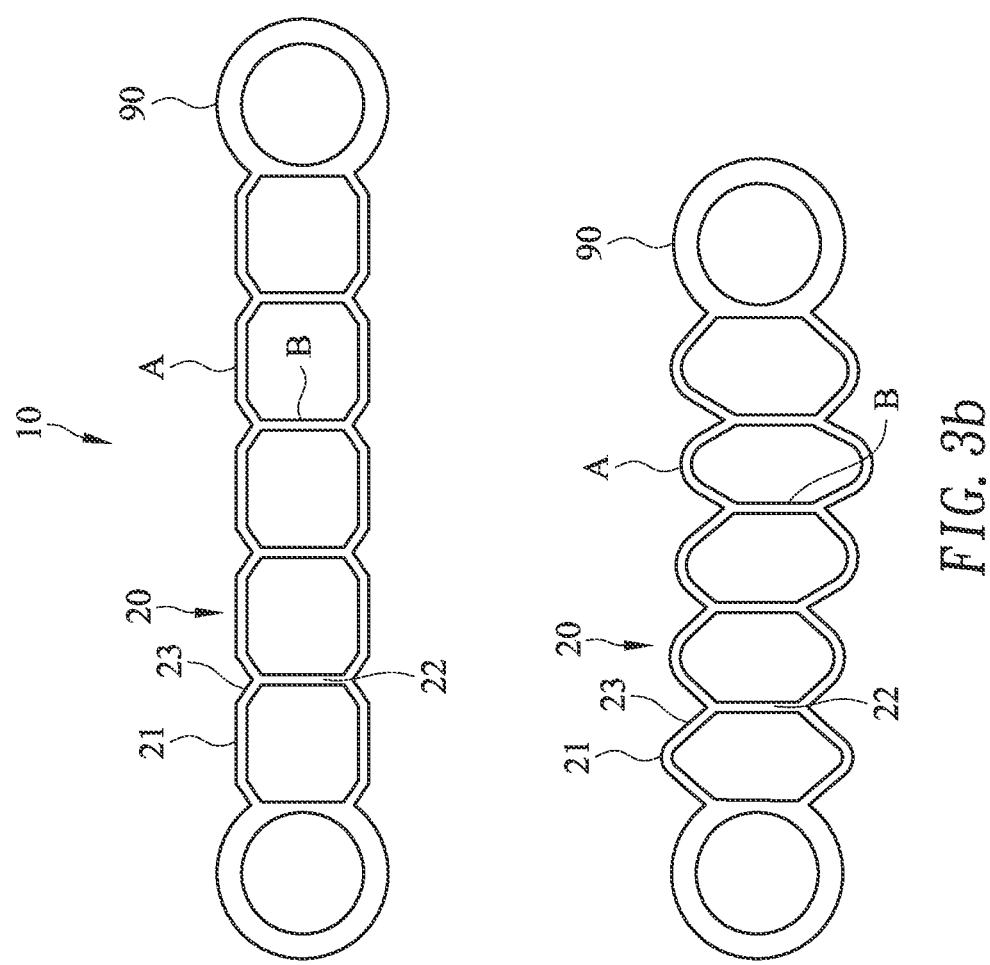
FIG. 3b shows the shortening of the bone plate shown in FIG. 2.

The inventive in-situ deformation of the bone plate shown in FIG. 2 are shown in FIGS. 3a to 3e, which includes
(1) Lengthening of the bone plate, as shown in FIG. 3a;
(2) Shortening of the bone plate, as shown in FIG. 3b;
(3) In-plane bending of the bone plate, as shown in FIG. 3c;
(4) Out-of-plane bending of the plate, as shown in FIG. 3d;
(5) Twisting of the plate (Rotating the plate about plate axis), as shown in FIG. 3e.

The bone plate of the present invention may further comprise at least one branch/arm to facilitate fixing multiple fractures.

The inventive bone plate can be made from any material that may facilitate the desired deformation in-situ. Preferably, the bone plate material has an ultimate tensile strength (UTS) that is higher than its yield strength (YS) by at least 20%, preferably by at least 30%, and more preferably by at least 40%.

Preferably, the bone plate material has a tensile elongation at least 10%, preferably at least 15%, and more preferably at least 20%.

Preferably, the bone plate is made from a biocompatible, metallic material.

Preferably, the bone plate is made from a metal of pure titanium, titanium alloy, pure iron, iron alloy, pure magnesium, magnesium alloy, pure zinc, zinc alloy, or a composite prepared from at least two of these metals. The inventive bone plates may be fabricated using any common techniques, such as casting, rolling, machining, electrically discharge machining, laser drilling, chemical etching, pressure molding, stamping, etc.

The invention claimed is:

1. A bone plate comprising a first elongated strip comprising a first series of repeating units, a first and a second terminal screw holes being provided at two ends of the first series of the repeating units, wherein the number of the repeating unit between the two terminal screw is about 2-20, and each repeating unit comprises two crowns, two necks, and four bridges, wherein the two crowns and the two necks are connected by the four bridges to from a ring structure, characterized in that a maximum distance between inner sides of the two crowns (ID) is greater than a width of the neck (NW), and a maximum distance between outer sides of two opposite bridges of the four bridges (OD) is greater than a unit length between two adjacent repeating units (UL), which is a distance between centers of two neighboring ring structures.

2. The bone plate according to claim 1, wherein a width of the bridge (BW) is greater than a width of the crown (CW).

3. The bone plate according to claim 1, wherein an outer side of each of the two crowns of the repeating unit is faceted.

4. The bone plate according to claim 1, wherein inner sides of each of the two necks of the repeating unit are faceted.

5. The bone plate according to claim 1 further comprising a second elongated strip with one end thereof extending or branching from the first elongated strip and with another end thereof being provided with a third terminal screw hole, wherein the second elongated strip comprises a second series of the repeating units between the first elongated strip and the third terminal screw hole.

6. The bone plate according to claim 1 further comprising a second elongated strip with one end thereof extending or branching from the first elongated strip and with another end thereof being provided with a third terminal screw hole; and a third elongated strip with one end thereof extending or branching from the first elongated strip and with another end thereof being provided with a fourth terminal screw hole, wherein the second elongated strip comprises a second series of the repeating units between the first elongated strip and the third terminal screw hole, and the third elongated strip comprises a third series of the repeating units between the first elongated strip and the fourth terminal screw hole.

7. The bone plate according to claim 5, wherein the second elongated strip and the first elongated strip have a common longitudinal axis.

8. The bone plate according to claim 5, wherein the first elongated strip has a first longitudinal axis, and the second elongated strip has a second longitudinal axis, wherein the second elongated strip extends from one of the first or the second terminal screw hole with the first longitudinal axis and the second longitudinal axis forming an obtuse angle therebetween, or the first elongated strip and the second elongated strip form a shape similar to y.

9. The bone plate according to claim 6, wherein the first elongated strip, the second elongated strip and the third elongated strip form a shape similar to Y, X, T, + or π.

10. The bone plate according to claim 2, wherein the first elongated strip has a thickness of about 0.1-2.5 mm, the CW is about 0.1-1.0 mm, the BW is of about 0.2-3.5 mm, the ID is of about 1-8 mm, the NW is about 0.5-5 mm, the OD is about 1.5-15 mm, and the UL is about 1-10 mm.

11. The bone plate according to claim 10, wherein the first elongated strip has a thickness of about 0.5-1.5 mm, the CW is about 0.1-0.5 mm, the BW is of about 0.2-2 mm, the ID is of about 2-4 mm, the NW is of about 1-3 mm, the OD is of about 2.5-5 mm, and the UL is of about 2-5 mm.

12. The bone plate according to claim 1, wherein the first elongated strip is made of a metal of pure titanium, titanium alloy, pure iron, iron alloy, pure magnesium, magnesium alloy, pure zinc, zinc alloy, or a composite prepared from at least two of these metals.

13. A method of deforming a bone plate as defined in claim 1, which comprises shortening the bone plate or lengthening the bone plate, wherein said shortening the bone plate comprises the following steps:

squeezing the ring structure of one repeating unit of the first series of the repeating units by clamping the two necks of the ring structure, so that the two crowns between the clamped two necks are arched in a direction perpendicular to a longitudinal axis of the first elongated strip and on a same plane of the first elongated strip; and repeating the squeezing step to another repeating unit of the first series of the repeating units until a desired number of the repeating units of the first series of repeating units are squeezed; and said lengthening the bone plate comprises the following steps:

flattening the ring structure of one repeating unit of the first series of the repeating units by clamping the two crowns of the ring structure, so that the clamped two crowns and the four bridges of the same ring structure are flattened on a same plane of the first elongated strip; and repeating the flattening step to another repeating unit of the first series of the repeating units until a desired number of the repeating units of the first series of repeating units are flattened.

14. The method according to claim 13 further comprising bending the bone plate, or twisting the bone plate, wherein said bending the bone plate comprises the following steps:

inserting three posts into three ring structures of the first series of the repeating units; and pulling two end posts of the three posts in a first direction perpendicular to a longitudinal axis of the first elongated strip and on a same plane of the first elongated strip and simultaneously pushing a middle post of the three posts in a second direction opposite to the first direction, so that the two crowns of the ring structure receiving the middle post are bended; and said twisting the bone plate comprises the following steps:

clamping both ends of the first elongated strip; and rotating one end of the first elongated strip while holding another end thereof still, so that the first elongated strip is twisted.

* * * * *